US011168873B2

(12) United States Patent
Strelchuk et al.

(10) Patent No.: US 11,168,873 B2
(45) Date of Patent: Nov. 9, 2021

(54) ILLUMINATION SYSTEM CONTROLLER FOR AIMING LIGHT FIXTURES IN SANITARY ENVIRONMENTS

(71) Applicant: THE KIRLIN COMPANY, Detroit, MI (US)

(72) Inventors: Joseph Strelchuk, Clarkston, MI (US); Stephen C. Brownell, Grosse Pointe Farms, MI (US)

(73) Assignee: THE KIRLIN COMPANY, Detroit, MI (US)

( * ) Notice: Subject to any disclaimer, the term of this patent is extended or adjusted under 35 U.S.C. 154(b) by 196 days.

(21) Appl. No.: 16/407,373

(22) Filed: May 9, 2019

(65) Prior Publication Data

US 2020/0355355 A1 Nov. 12, 2020

(51) Int. Cl.
*A61B 90/30* (2016.01)
*F21V 21/15* (2006.01)
*G06F 3/0488* (2013.01)
*G06F 3/0484* (2013.01)
*H04N 7/18* (2006.01)
*F21W 131/205* (2006.01)

(52) U.S. Cl.
CPC ............ *F21V 21/15* (2013.01); *A61B 90/30* (2016.02); *G06F 3/04847* (2013.01); *G06F 3/04886* (2013.01); *A61B 2560/0487* (2013.01); *F21W 2131/205* (2013.01); *H04N 7/181* (2013.01)

(58) Field of Classification Search
CPC .......... F21V 21/15; A61B 90/30; A61B 90/35
USPC ........................................................ 362/33
See application file for complete search history.

(56) References Cited

U.S. PATENT DOCUMENTS

| | | | |
|---|---|---|---|
| 5,526,245 A | 6/1996 | Davis et al. | |
| 6,820,999 B2 * | 11/2004 | Kotovsky | F21V 21/34 362/233 |
| 7,321,385 B2 * | 1/2008 | Rus | H04N 5/23216 348/69 |
| 10,231,607 B2 * | 3/2019 | Charles | A61B 1/051 |
| 10,517,158 B2 * | 12/2019 | Hallack | H05B 47/125 |
| 2011/0146676 A1 * | 6/2011 | Dallam | E04B 9/006 128/203.12 |
| 2015/0055323 A1 * | 2/2015 | Schreiber | F21V 21/30 362/96 |
| 2017/0127909 A1 * | 5/2017 | Prendergast | A61B 1/0684 |
| 2018/0116754 A1 * | 5/2018 | Hollopeter | F21V 21/04 |
| 2019/0249847 A1 * | 8/2019 | Hallack | F21V 14/02 |

OTHER PUBLICATIONS

Website Skytron, LLC.—Specialty Lights, www.skytron.us/products/pages/specialty.html, Copyright Skytron 2017, retrieved on Apr. 24, 2017, 1 page.

(Continued)

*Primary Examiner* — Christopher M Raabe
(74) *Attorney, Agent, or Firm* — Brooks Kushman P.C.

(57) ABSTRACT

An illumination system controller with one or more touch screen controllers for aiming light fixtures in sanitary environments. The system has (1) one or more light fixtures; (2) one or more touch screen controllers in communication with one or more light fixtures; and (3) software in communication with a touch screen controller and a light fixture that is adapted to aim light beam direction.

13 Claims, 3 Drawing Sheets

(56) References Cited

OTHER PUBLICATIONS

Website Skytron, LLC.—Lucina 4, www.skytron.us/products/pages/lucina4.html, Copyright Skytron 2017, retrieved on Apr. 24, 2017, 1 page.
Maquet Medical Systems USA, PowerLED: The 2nd Second Generation is Here!, Copyright Maquet SAS, Ardon, Printed in USA Jan. 2013, 12 pages.
Tthe Kirlin Company, OPTeMED 1 Light System 360—MRR-12642, Aug. 2018, 4 pages.
The Kirlin Company, INFRALED® 60 Lighting in Birthing Suites, Oct. 2015, 2 pages.

* cited by examiner

ILLUMINATION SYSTEM CONTROLLER FOR AIMING LIGHT FIXTURES IN SANITARY ENVIRONMENTS

TECHNICAL FIELD

In at least one aspect, the present invention is related to one or more touch screen controllers for aiming one or more light fixtures in an illumination system that is deployed in a sanitary environment.

BACKGROUND

In some sanitary environments, an operator is challenged with determining how to effectively direct light beams from an illumination system in such a way that the beams are accurately aimed on a task site (e.g., a zone of interest on a patient in an operating room) without using any methods (e.g., physical contact with a light fixture) or introducing any devices (e.g., a wand) that could introduce or spread contamination.

Ideally, acceptable solutions to the problem of aiming lighting in such an environment require immediate and precise control of light fixtures, perhaps involving re-positioning or tilting one or more light fixtures, with minimal interaction from the operator.

Existing control methods may require the operator to manually move the light fixtures or push buttons or flip switches by a foot or hand, which may or may not be sanitary.

In the operating theater, precisely trained illumination is needed for safe surgery and effective patient treatment. Ideally, light beams are quickly and accurately aimed. Preferably, they should be so directed as to avoid casting a shadow.

SUMMARY

One aspect of this disclosure allows an operator to control an illumination system without compromising a sanitary environment (such as an operating room) by using one or more control subsystems, which may include a touch screen controller and software executable thereon. Optionally the touch screen controller could be associated with a device that is mounted on a fixed or movable substrate (e.g., a table or a wall or a portable board). A motorized feature is associated with one or more of the light fixtures. The motorized feature includes a receiver that recognizes and responds to signals that are generated by software running on a microprocessor affiliated with a touch screen controller.

Using such a subsystem, it would be desirable to be able to activate and/or move (collectively, "control") one or more lights or groups of lights in the illumination system that are usually ceiling- or wall-mounted. The subsystem controls some or all individual light fixtures or groups in response to a location specified by an operator who touches a screen on the touch pad controller at a location on an image of for example a patient to which light beams are to be aimed.

It would be desirable to produce such results with ease, predictability and precision. For example, upon touching the screen at a point on an image of the patient, light beams in a precisely defined incident path may be trained on, for example a specific corresponding location on the patient in an operating room. Once suitably directed, the light fixture(s) are aimed at the target location without the need for additional interactions.

In some applications outside an operating room environment, for example a clean room in a facility where electronic components are assembled, different terminology may be used. In such contexts, a "workpiece" may be considered in this disclosure as being substantially equivalent to the "patient" in an operating room.

In several embodiments, one or more of the controllable illumination systems include (1) one or more electromechanically energized light fixtures mounted in a ceiling or wall for re-positioning or tilting; and (2) a one or more control subsystems with
   a touch screen controller in wired or wireless communication with one or more of the light fixtures and/or groups thereof; and
   a touch screen with an image of the patient or workpiece;
   software in communication with the touch screen controller that is adapted to influence one or more light fixture characteristics, including its off/on state and beam direction of a beam that emanates from a light fixture or group thereof; and (3) optionally, one or more ceiling-mounted or wall-mounted cameras.

In a hospital or outpatient environment, the patient—or in an electronic assembly facility the workpiece—under examination is positioned on a table or a similar platform ("task site"). The operator will select the desired number of light fixtures to be activated and the location to which they are to be directed by touching a screen or pad. Hereinafter, "touch screen" is used interchangeably with "touch screen controller". Optionally additional touch screen controllers may be deployed.

In an alternative embodiment, light selection, state (On/Off) and movement may be influenced and specified by voice activation.

Preferably, the touch screen controller(s) are positioned outside the sanitary field. The actions performed by the operator are performed quickly and easily. Further, the chance of introducing contamination into the sanitary field is virtually eliminated.

DETAILED DESCRIPTION

Figure 1:
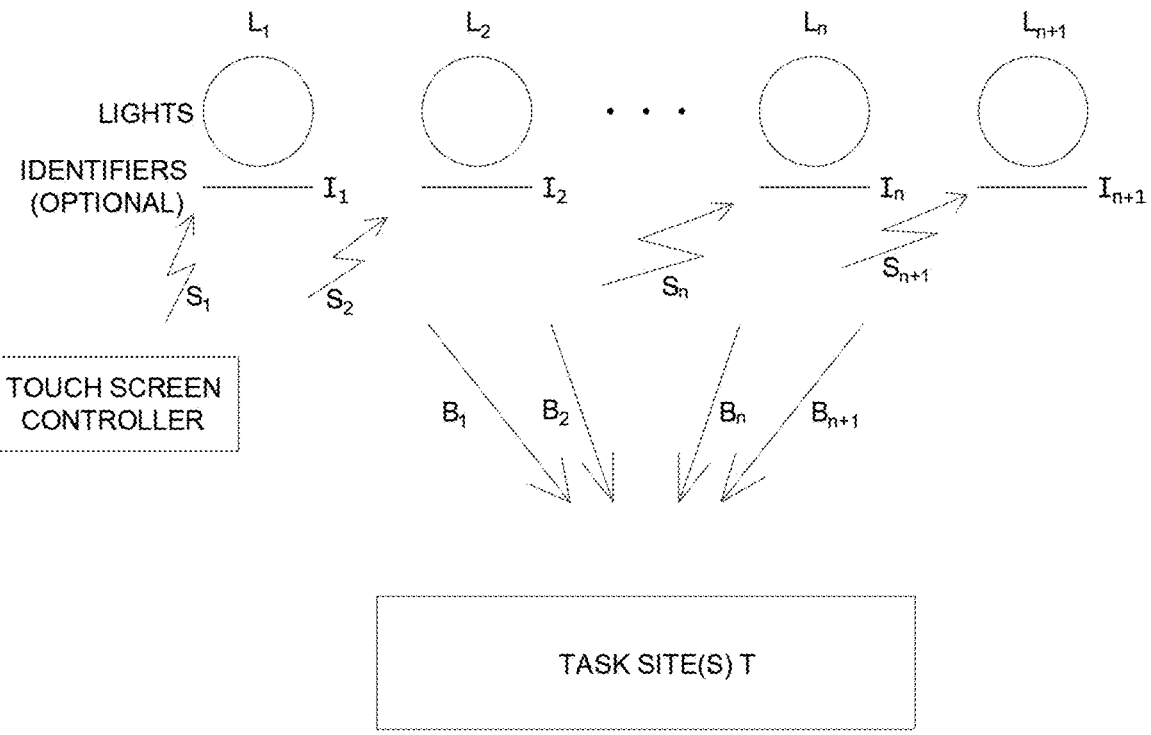
FIG. 1 is a schematic illustration of a representative illumination system layout, which includes a touch screen controller in communication with one or more light fixtures.

As required, detailed embodiments of the present invention are disclosed herein; however, it is to be understood that the disclosed embodiments are merely exemplary of the invention that may be embodied in various and alternative forms. Reference will now be made in detail to presently preferred embodiments and methods of the present disclosure, which constitute the best modes of practicing the invention presently known to the inventors.

The Figures are not necessarily to scale and some features may be exaggerated or minimized to show details of particular components. Specific details disclosed herein are not to be interpreted as limiting, but merely as a representative basis for any aspect of the invention and/or as a representative basis for teaching one skilled in the art to variously employ the present invention.

It must also be noted that, as used in the specification and the appended claims, the singular form "a," "an," and "the" comprise plural references unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

Throughout this application, where publications or brochures or websites describing product names are referenced, the disclosures of these publications or brochures in their entireties are hereby incorporated by reference into this application to more fully describe the state of the art to which this invention pertains.

Several embodiments of this disclosure address the challenges of providing a versatile lighting system, primarily but not exclusively for use in sanitary environments. Desirably, an optimal illumination system is such that operation of light fixtures does not introduce or spread contamination, while being able to deliver high quality shadow-less light. Representative environments of use include but are not limited to an operating room in a hospital or a clean room in which electronic components are assembled.

Usually, the light fixtures of an illumination system are located on a wall or at the ceiling line of for example an operating theater and lie away from the operator, thus avoiding the casting of shadows.

Preferably, one or more touch screen controllers (FIGS. 1-2) are provided. The touch screen controllers may be wall or board-mounted or be mobile, perhaps in the form of a tablet (collectively, "touch screen controllers"). In use, one or more touch screen controllers communicate wirelessly via a Bluetooth signal with a sensor or receiver associated with a motorization feature of a light fixture. The one or more touch screen controllers include software that produces signals to the motorized features associated with the light fixtures.

In some embodiments, a group of light fixtures may be moved by one motorized feature. In other embodiments, each light fixture has its own motorized feature.

The signals ($S_s$, FIG. 2) from an exemplary touch screen controller to a light fixture activate (i.e., turn on or off) a motorized feature associated with a light fixture. A signal ($S_m$) causes the light fixture to move to a position specified by an operator. Similarly for a group of light fixtures in an array if desired. Thus configured, the control subsystem in an illumination system allows an operator by touching the touch screen controller to activate the light fixture(s) and/or adjust the position of beams from one or more light fixtures by tilting the associated fixtures.

The desired illumination to be cast in the environment of use (e.g., an operating room in a hospital) depends on the demands of the varied tasks to be performed (e.g., a medical procedure—or an assembly step performed in a clean room of a laboratory or electronics assembly facility). Optionally, the beams from the light fixtures may be directed in various alternative positions, depending on the task to adequately illuminate a patient or work site and avoid the casting of shadows.

As noted above, a single illumination system may include one or more groups of light fixtures. Thus, one or more control subsystems may influence the beam characteristics (e.g., ON/OFF, direction) of each or all fixtures in a group. In this way, for example, a single command may cause each light fixture in a group to emit a beam that has characteristics identical to other light fixtures in that group. In alternative embodiments, a given light fixture may include several individual light sources.

In one exemplary embodiment, an illumination system may include a plurality of motorized light fixtures mounted in and above a ceiling so that they are recessed. One or more light fixtures include a motorized aiming system that allows the light fixture and thus the beam that emanates therefrom to be directed as desired towards the patient or worksite. Thus, for example a light fixture may move or tilt above the plane of a ceiling so that a resultant beam can be repositioned as needed.

One or more of the light fixtures connect to one or more touch screen controllers via wireless or cabled means. The touch screen controller may for example be embodied in a central control panel and communicate with the light fixtures via one or more cables which coordinate beam characteristics (e.g., OFF/ON, direction) in response to touch commands entered on the touch screen.

It will be appreciated that the subject under examination is located on a table or similar ("task site"). In use, the operator will turn on the illumination system by for example flipping a switch or by a touch command entered on the touch screen controller and will aim the light fixtures to their desired location.

FIG. 1 schematically depicts the above-described light fixtures $L_1, L_2 \ldots L_n, L_{n+1}$ and their associated motorized features or a group thereof in an illumination system. In an alternative embodiment, one or more of the light fixtures are associated with a respective status identifier $I_1, I_2 \ldots I_n, I_{n+1}$ (e.g., a blue ring that encircles the light fixture). In the control subsystem, the touch screen controller sends one or more signals $S_1, S_2 \ldots S_n, S_{n+1}$ respectively to the motorized features associated with the light fixtures $L_1, L_2 \ldots L_n, L_{n+1}$.

Figure 2:
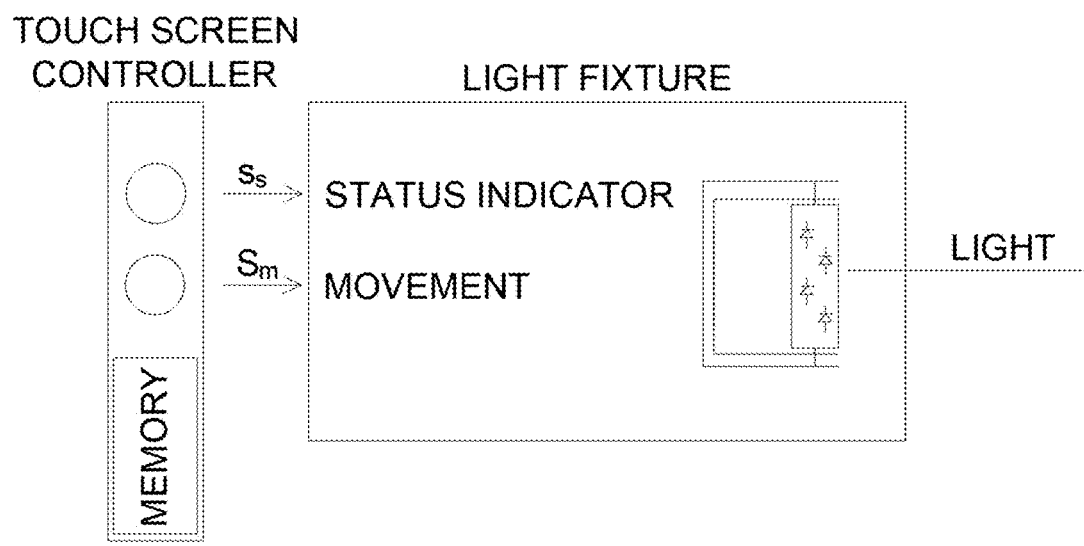
FIG. 2 shows exemplary signal flow paths between a touch screen controller and a representative light fixture/motorized feature combination.
Figure 3:
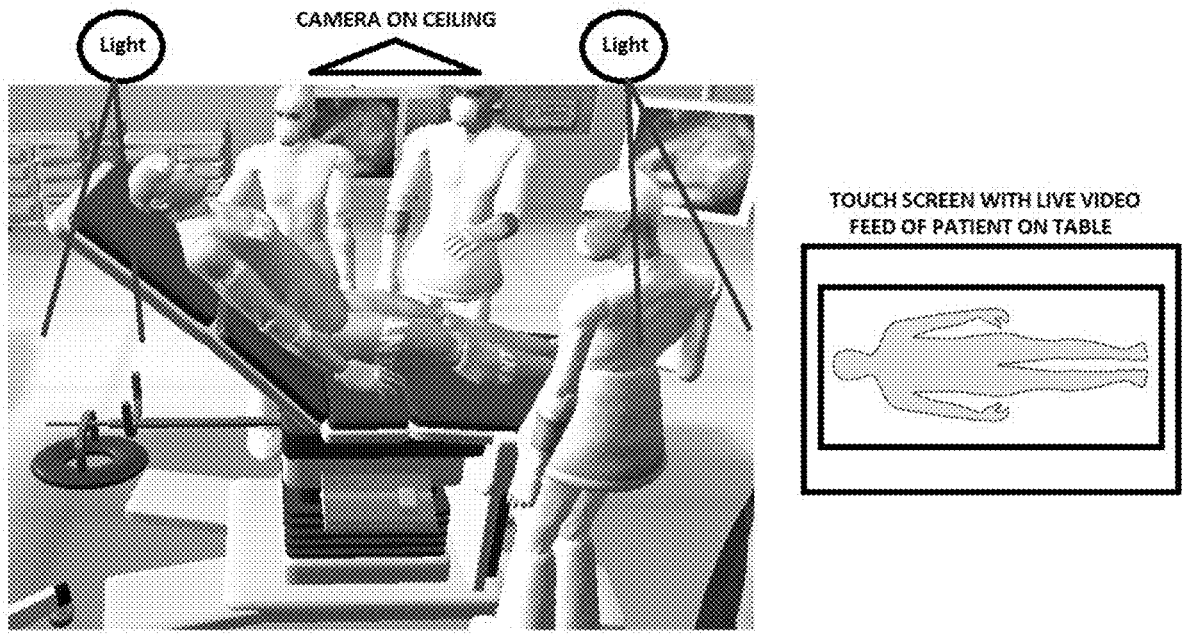
FIG. 3 shows a patient located on a procedure table ("task site") whose image appears on a touch screen controller.
Figure 4:
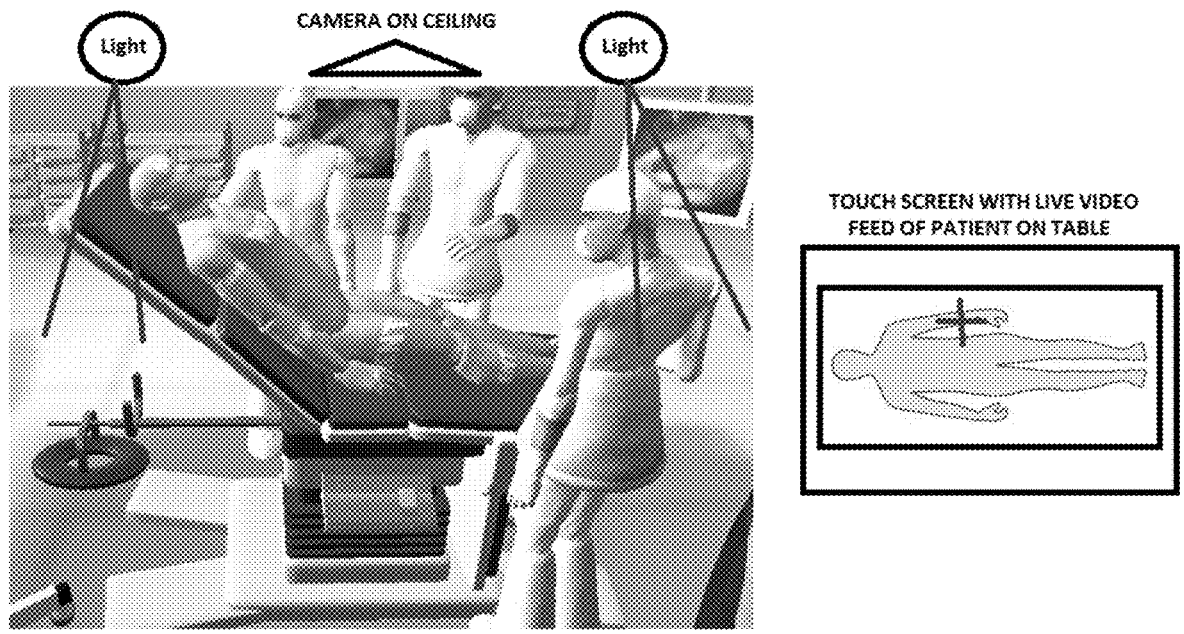
FIG. 4 shows how an operator may aim a light beam towards a specific location on the patient by touching a corresponding position on the touch screen controller.
Figure 5:
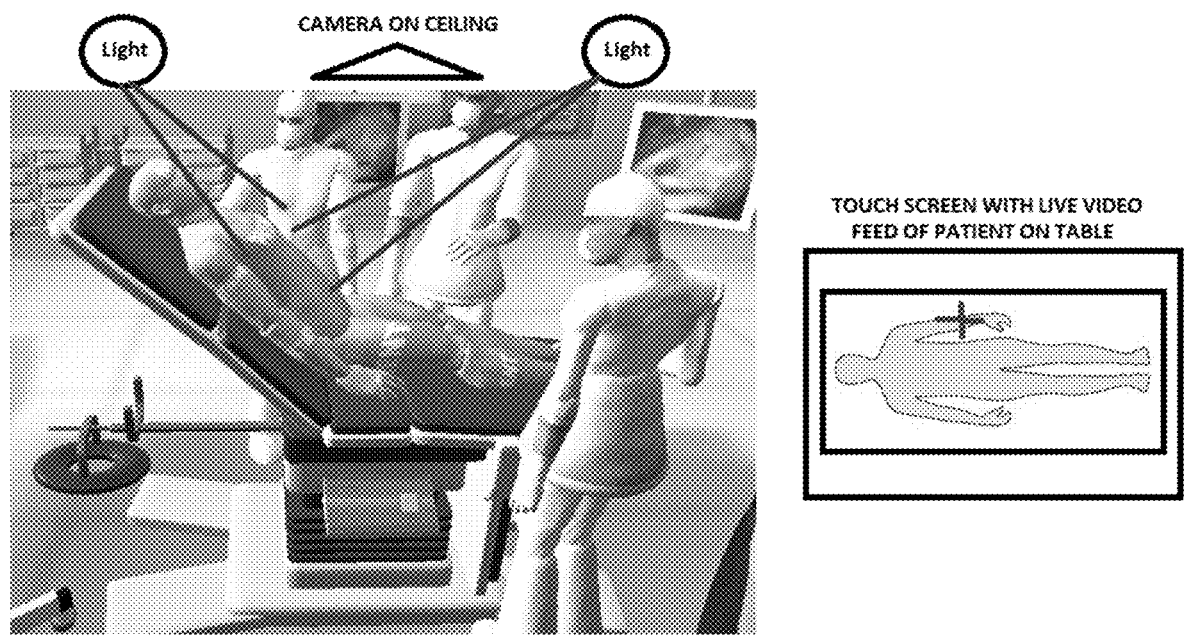
FIG. 5 suggests how one or more light fixtures automatically move so as to direct light beams to the specified location(s) on the patient in response to the operator's touch command entered on the touch screen.

Consider in FIG. 2 a signal $S_s$ that its transmitted from a touch screen controller to a light fixture. That signal may be considered to represent constituent signals that influence a desired state (ON/OFF) or a desired target locator (perhaps defined by a real or imagined Cartesian coordinates x,y on the screen) which is selected by the operator when he/she touches an aim point on the touch screen. Alternatively, the aiming position may be determined by voice command, e.g., "Move to [position] A, B . . . (etc)".

In some embodiments, the touch screen controller transmits exemplary signals $S_s$ (ON/OFF status) to a light fixture and $S_m$ (movement) to a motorized feature associated with the light fixture $L_n$. Such signals may be transmitted from the touch screen controller along strands of a hard-wired cable or be communicated wirelessly by individual signals corresponding to $S_a$, and $S_m$, each having unique characteristics (e.g., wavelength or frequency, etc.).

The motorized features include a sensor or receiver associated with one or more light fixtures to be controlled. In this context, the light fixture may be termed an "intelligent" light fixture. Each intelligent light fixture receives those signals and activates or moves an associated light fixture, bulb, LED or other light source. Such signals may be discrete (e.g., ON/OFF) or be analog (e.g., low/medium/high, etc). As used herein the term "activates" includes ON/OFF and beam re-direction.

To enable the above-described features, software in the form of an app may run on the touch screen controller to generate signals in response to an operator's touch. Corresponding software and circuitry including one or more microprocessors are provided on one or more of the touch screen controllers to generate those signals. Optionally some of the circuitry associated with the touch screen controller may reside in for example a circuit board in a ceiling to be juxtaposed with a motorized feature and/or a light fixture. Such an illumination system configuration dispenses with a wall-mounted touch screen controller.

In summary,

A. $S_s$ symbolizes a command signal that turns the light fixture on and off; and B. $S_m$ symbolizes a command signal that synchronizes with for example a motorized feature that displaces or repositions or tilts an LED source and/or a reflector associated therewith so that the LED source may aim a beam along a desired path.

Advantages of several embodiments of the illumination system include:

A. Ease of control by the operator without incursion into or compromising a sanitary field;

B. Shortened time required by the operator to specify or alter lighting characteristics; and C. Capability to move light fixtures individually or as a group.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A controllable illumination system comprising:
one or more light fixtures that are adaptable to cast shadowless light, one or more of the one or more light fixtures including associated motorized features; and
one or more control subsystems having:
a touch screen controller located outside a sanitary field in communication with one or more of the motorized features, the touch screen controller including a screen that portrays an image of a patient or workpiece reposed on a task site, so that an operator may specify an aiming location at which one or more light beams or light fixtures in a group of light fixtures may be aimed; and
software running on an associated touch screen controller that is adapted to communicate command signals from the touch screen controller to one or more of the one or more light fixtures and/or associated motorized features, the command signals being adapted to influence one or more light fixture characteristics in response to a position-determining command entered by an operator touching the touch screen controller, the characteristics including beam direction of beams that emanate from a light fixture or group of light fixtures, the controllable illumination system also having one or more cameras in communication with one or more of the one or more touch screen controllers so that a real-time or static image of a patient or work piece at the task site is captured by one or more of the one or more cameras and transmitted to one or more of the one or more touch screen controllers to facilitate viewing by an operator and aiming of emergent beams.

2. The controllable illumination system of claim 1 wherein
at least one of the one or more associated motorized features are adapted to reposition a light fixture that is movable in response to the position-determining command,
the position-determining command including a position selected by the operator on an image of a patient or workpiece on the touch screen controller,
the touch screen controller transmitting a signal $S_m$ to one or more of the one or more motorized features of associated light fixtures, thus directing one or more light beams that emanate from one or more of the one or more light fixtures.

3. The controllable illumination system of claim 1 wherein the touch screen controller is wall-mounted.

4. The controllable illumination system of claim 2 wherein there is a wired communication link between the touch screen controller and one or more of the motorized features.

5. The controllable illumination system of claim 2 wherein there is a wireless communication between the touch screen controller and one or more of the motorized features.

6. The controllable illumination system of claim 1, wherein
a single controllable illumination system includes one or more groups of light fixtures so that one or more of the touch screen controllers are adapted to influence the beam characteristics of each fixture in a group and so that a single command entered on the touch screen controller may cause each light fixture in the group to emit a beam that has directional characteristics identical to other light fixtures in that group.

7. The controllable illumination system of claim 1, wherein the illumination system includes one or more motorized light fixtures mounted in a ceiling or wall, one or more of the one or more motorized light fixtures having a tilting system that allows the associated light fixture to be selectively directed towards a patient or task site, the associated light fixture being recessed so that it moves above the plane of a ceiling or spaced apart from and within a wall.

8. The controllable illumination system of claim 2, wherein one or more of the one or more cameras are ceiling-mounted.

9. The controllable illumination system of claim 1, wherein the one or more of the one or more touch screen controllers located outside a sanitary field reduce the chance of introducing contamination into the sanitary field.

10. The controllable illumination system of claim 1 wherein
one or more of the one or more light fixtures transmit a signal $S_s$ to one or more of the one or more touch screen controllers, thus indicating a status of one or more of the one or more light fixtures.

11. The controllable illumination system of claim 10, wherein the status of one or more of the one or more light fixtures is (A) on/off and (B) selected by one of the one or more touch screen controllers or not.

12. The controllable illumination system of claim 1, wherein one or more of the one or more touch screen controllers includes a memory function that allows beam positioning to be stored for later retrieval.

13. A method for controlling an illumination system comprising the steps of:
(A) installing one or more light fixtures so that they cast shadowless light, cameras and associated motorized features in a support structure such as a ceiling or a wall;
(B) positioning one or more touch screen controllers outside a sanitary field and communicating the one or more touch screen controllers with one or more of the one or more light fixtures, cameras and associated motorized features; and
(C) running software that generates command signals in communication with one or more of the one or more touch screen controllers and one or more of the one or more motorized features of the one or more light fixtures and cameras, the command signals being adapted to aim the direction of beams that emanate from a light fixture and cameras towards a patient or workpiece at a task site.

* * * * *